US008624185B2

(12) United States Patent
Maas et al.

(10) Patent No.: US 8,624,185 B2
(45) Date of Patent: Jan. 7, 2014

(54) SAMPLE PREPARATION

(75) Inventors: Diederik Jan Maas, Breda (NL); Maria Rudneva, Delft (NL); Emile van Veldhoven, Den Hoorn (NL); Hendrik Willem Zandbergen, Katwijk (NL)

(73) Assignee: Carl Zeiss Microscopy, LLC, Thornwood, NY (US)

( * ) Notice: Subject to any disclaimer, the term of this patent is extended or adjusted under 35 U.S.C. 154(b) by 0 days.

(21) Appl. No.: 13/233,397

(22) Filed: Sep. 15, 2011

(65) Prior Publication Data
US 2012/0199737 A1      Aug. 9, 2012

Related U.S. Application Data

(60) Provisional application No. 61/384,035, filed on Sep. 17, 2010.

(51) Int. Cl.
*H01J 37/30* (2006.01)
(52) U.S. Cl.
CPC ..................................... *H01J 37/30* (2013.01)
USPC ..................................... 250/309; 250/492.21
(58) Field of Classification Search
USPC ..................... 250/309, 492.21, 311
See application file for complete search history.

(56) References Cited

U.S. PATENT DOCUMENTS

| 5,656,811 | A  | * | 8/1997  | Itoh et al. ........................ 850/43 |
| 6,570,170 | B2 |   | 5/2003  | Moore |
| 7,002,152 | B2 | * | 2/2006  | Grunewald .................... 250/311 |
| 7,112,790 | B1 | * | 9/2006  | Wang ............................. 250/307 |
| 7,485,873 | B2 |   | 2/2009  | Ward et al. |
| 7,659,506 | B2 |   | 2/2010  | Avinun-Kalish et al. |
| 7,845,245 | B2 | * | 12/2010 | Hayles et al. .............. 73/864.91 |
| 7,952,083 | B2 | * | 5/2011  | Shichi et al. ................ 250/492.3 |

OTHER PUBLICATIONS

Jian Li et al., "Recent advances in FIB-TEM specimen preparation techniques," *Materials Characterization* 57(1): 64-70 (2006).
Y.S. Hor et al., "Superconductivity in CuxBi2Se3 and its Implications for Pairing in the Undoped Topological Insulator," Phys. Rev. Left. 104, 057001 (2010).
Rudneva et al., "Preparation of electron transparent samples of preselected areas using a Helium Ion Microscope," Conf. Proceedings of International Microscopy Congress 17, Rio de Janeiro, Brazil, (eds. G. Solorzano and W. de Souza), p. 118.18 (Sep. 19-24, 2010).

* cited by examiner

*Primary Examiner* — Kiet T Nguyen
(74) *Attorney, Agent, or Firm* — Fish & Richardson P.C.

(57) ABSTRACT

Disclosed are methods for preparing samples that include forming a first channel in a material by directing a first plurality of noble gas ions at the material, forming a second channel in the material by directing a second plurality of noble gas ions at the material, where the second channel is spaced from the first channel so that a portion of the material between channels has a mean thickness of 100 nm or less, and detaching the portion from the material to yield the sample.

20 Claims, 6 Drawing Sheets

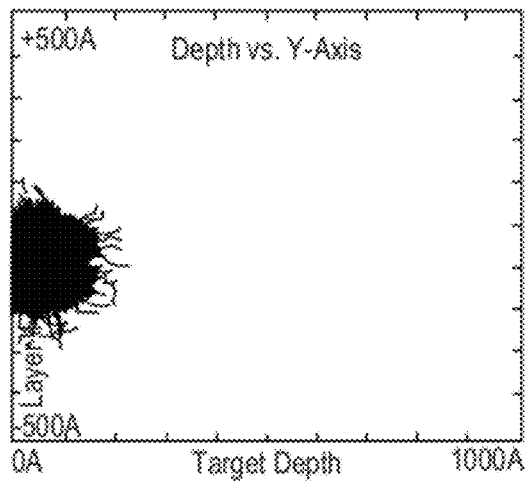
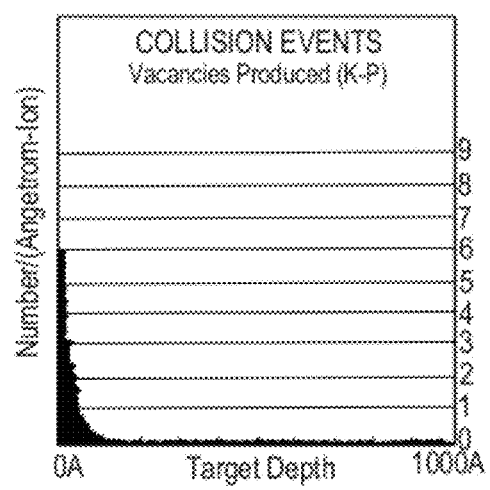
FIG. 1A     FIG. 1B
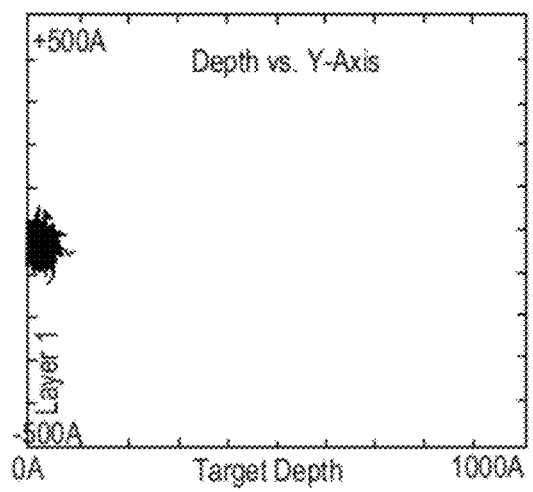
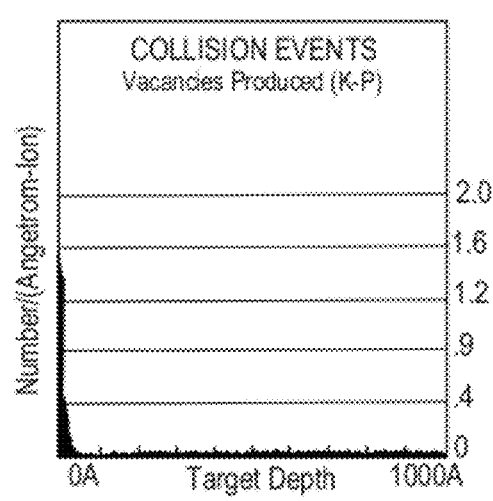
FIG. 2A     FIG. 2B

SAMPLE PREPARATION

CROSS-REFERENCE TO RELATED APPLICATIONS

This application claims priority under 35 U.S.C. §119(e)(1) to U.S. Provisional Application No. 61/384,035 filed Sep. 17, 2010. The contents of this application is hereby incorporated by reference in its entirety.

TECHNICAL FIELD

This disclosure relates to preparation of samples for examination in microscopes such as transmission electron microscopes.

BACKGROUND

Transmission electron microscopy can yield information about sample structure. In transmission electron microscopes (TEMs), a beam of electrons is incident on a first sample surface, and electrons leaving a second sample surface (e.g., opposite the first surface) are detected.

SUMMARY

In general, in a first aspect, the disclosure features methods of preparing a sample that include forming a first channel in a material by directing a first plurality of noble gas ions at the material, forming a second channel in the material by directing a second plurality of noble gas ions at the material, where the second channel is spaced from the first channel so that a portion of the material between channels has a mean thickness of 100 nm or less, and detaching the portion from the material to yield the sample.

In another aspect, the disclosure features methods of preparing a sample that include exposing a material to noble gas ions by directing a plurality of the noble gas ions at the material to form a channel in the material, the channel having a bottom wall oriented in a plane perpendicular to a direction of incidence of the noble gas ions on the material, and stopping the exposing when a mean thickness of the bottom wall of the channel, measured in a direction parallel to the direction of incidence, is less than 100 nm.

In a further aspect, the disclosure features methods that include using a noble gas ion beam to form a first channel and a second channel in a surface of a material, a portion of the material positioned between the channels having a mean thickness of 100 nm or less, detaching the portion of the material, exposing a first surface of the detached portion to a plurality of charged particles, and detecting particles leaving a second surface of the detached portion opposite to the first surface.

In another aspect, the disclosure features methods that include using a noble gas ion beam to form a channel in a surface of a material, the channel including a bottom wall with a mean thickness of 100 nm or less, exposing a first surface of the bottom wall to a plurality of charged particles, and detecting particles leaving a second surface of the bottom wall opposite to the first surface.

Embodiments of the methods can include any one or more of the following features.

The sample can be a transmission microscopy sample.

The first plurality of noble gas ions can be incident on the material at an angle of 10 degrees or less (e.g., 5 degrees or less) relative to a surface normal of the material. The second plurality of noble gas ions can be incident on the material at an angle of 10 degrees or less (e.g., 5 degrees or less) relative to a surface normal of the material.

The mean thickness of the sample can be 50 nm or less (e.g., 20 nm or less). A mean energy of the first plurality of noble gas ions can be 30 keV or more. A mean energy of the first plurality of noble gas ions can be 15 keV or less. A mean energy of the second plurality of noble gas ions can be 30 keV or more. A mean energy of the second plurality of noble gas ions can be 15 keV or less.

Detaching the portion from the material can include contacting a first region of the portion with an extended member. Detaching the portion from the material can include applying a force to the portion with the extended member. The extended member can include a needle. The needle can be formed of at least one of glass and tungsten. The method can include contacting the detached portion with a carbon-based grid material.

The method can include heating the material prior to detaching the portion. The material can be heated to a temperature of 100° C. or more for a period of 5 minutes or more prior to detaching the portion.

A mean energy of the plurality of noble gas ions can be 30 keV or more. A mean energy of the plurality of noble gas ions can be 15 keV or less.

The method can include positioning the material on a carbon-based grid material.

The method can include monitoring the mean thickness of the bottom wall during the exposing. The monitoring can include detecting noble gas ions that are transmitted through the bottom wall during the exposing. The monitoring can include estimating the mean thickness of the bottom wall based on a measured ion current of the noble gas ions transmitted through the bottom wall. Alternatively, or in addition, the monitoring can include detecting secondary electrons that leave the sample during the exposing. The monitoring can include determining an energy distribution of the secondary electrons, and estimating the mean thickness of the bottom wall based on a width of the energy distribution.

The charged particles can include electrons and the detected particles can include electrons. The method can include determining, based on the detected electrons, at least one of structural information and compositional information for the material.

The noble gas ions can include helium ions. Alternatively, or in addition, the noble gas ions can include at least one (or more) of argon ions, neon ions, krypton ions, and xenon ions.

The method can include directing a plurality of electrons to be incident on the sample during formation of at least one of the first and second channels. The method can include directing a plurality of electrons to be incident on the sample during exposure of the material to the noble gas ions. The method can include directing a plurality of electrons to be incident on the sample during formation of the channel.

The method can include applying a voltage bias having a magnitude of 10 V or more relative to a common external potential ground to the sample during formation of at least one of the first and second channels. The method can include applying a voltage bias having a magnitude of 10 V or more relative to a common external potential ground to the sample during exposure of the material to the noble gas ions. The method can include applying a voltage bias having a magnitude of 10 V or more relative to a common external potential ground to the sample during formation of the channel.

Further, the methods can include any of the other steps and/or features disclosed herein, as appropriate.

Embodiments of the methods and systems can include any one or more of the following advantages.

In some embodiments, samples prepared using a noble gas ion beam include fewer dislocations and other irregularities in their crystal structures than they would if prepared by other methods including, for example, a gallium ion beam. As a result, measurements made on such samples are more accurate than measurements made on samples with a greater extent of disruption to their crystal structures.

In certain embodiments, samples can be prepared using the same instrument that is then used to investigate the samples. For example, the instrument can include both a noble gas ion beam for sample preparation, and an electron beam for sample investigation. This permits an accurate registration between the beam and the instrument to be maintained, and also permits measurements to be performed more rapidly than might otherwise be possible using a first instrument for sample preparation and a second instrument for sample investigation. Moreover, by not transferring the delicate samples from one instrument to another, sample integrity can more easily be maintained while avoiding sample damage.

In some embodiments, extremely thin samples can be prepared using a noble gas ion beam. For example, samples having thicknesses of 50 nm or less (e.g., 20 nm or less, 15 nm or less, 10 nm or less) can be prepared using a noble gas ion beam for sample processing. Using a heavier ion beam for sample processing could damage samples of these thicknesses; the lighter ions in a noble gas ion beam can cause less sample degradation during processing.

The details of one or more embodiments are set forth below. Other features and advantages will be apparent from the description, drawings, and claims.

DESCRIPTION OF DRAWINGS

FIG. 1A is a graph showing simulated high energy gallium ion beam trajectories in a platinum sample.

FIG. 1B is a graph showing number of vacancies produced per gallium ion per Angstrom as a function of depth for the gallium ions of FIG. 1A.

FIG. 2A is a graph showing simulated low energy gallium ion beam trajectories in a platinum sample.

FIG. 2B is a graph showing number of vacancies produced per gallium ion per Angstrom as a function of depth for the gallium ions of FIG. 2A.

Like reference symbols in the various drawings indicate like elements.

DETAILED DESCRIPTION

Figure 3:
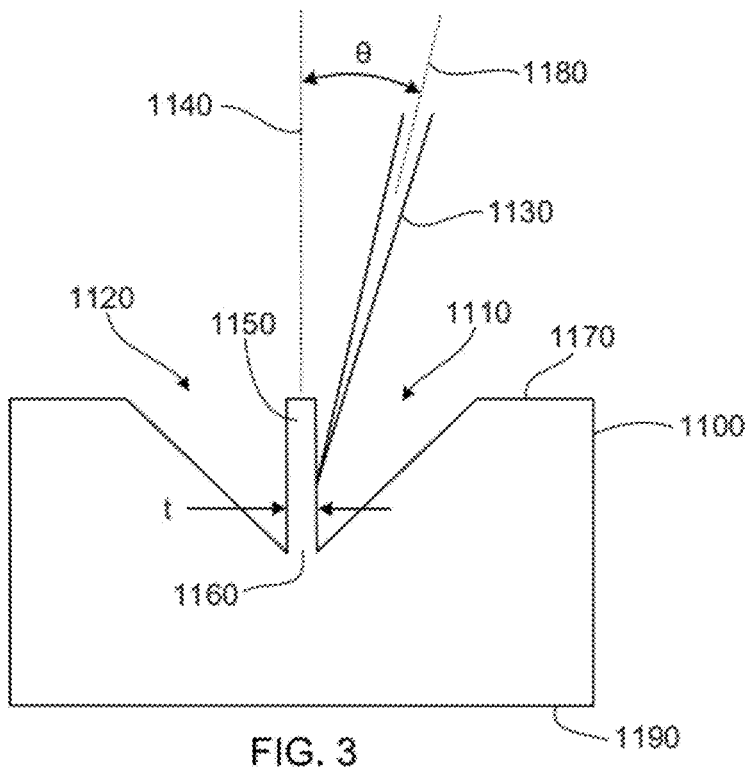
FIG. 3 is a schematic diagram showing a sample that is milled using a helium ion beam.

To investigate materials using transmission electron and transmission ion microscopy, thin lamellar samples of the materials are prepared and then exposed to a beam of electrons or ions. Producing a material sample that is sufficiently thin to allow electrons or ions to pass through the sample and be detected on the side opposite side is a delicate procedure. Typically, for example, to allow electrons to pass through the material, the sample has a thickness of 100 nm or less. At such small thicknesses, it can be difficult to both fabricate and handle samples without causing mechanical damage to the material.

One method that can be used to form transmission microscopy samples is to use a focused gallium ion beam to progressively thin a piece of material (e.g., by ion sputtering) to the desired thickness. In this method, the gallium ion beam is incident on the material surface to form two separate, closely-spaced channels that extend into the material. The material that remains between the channels constitutes the lamellar sample. The sample is progressively thinned by successive exposures to the gallium ion beam until the desired material thickness between the channels is reached. Then, the connection between the sample and the bulk material is severed and the thinned sample is lifted out and transferred to a TEM instrument. Ion milling is typically carried out with gallium ions having an average energy of approximately 30 keV.

Unfortunately, milling processes using gallium ions typically induce damage in the thinned sample by creating dislocations and other irregularities in the material's crystal structure. These irregularities can result in a "damage layer" of amorphous material on each surface of the sample that is exposed to the milling gallium ion beam. Damage layers can also include implanted gallium ions which contaminate the sample and further alter its natural crystal structure.

FIG. 1A shows the results of simulations that reveal the extent of sample damage as a result of gallium ion milling. In FIG. 1A, simulated ion trajectories in the lateral direction (e.g., along the surface of the milled sample) are shown as a function of depth extending into the sample. FIG. 1B includes simulation results showing the number of vacancies per incident gallium ion produced in the crystal structure of the material as a function of depth extending into the sample. As shown in FIGS. 1A and 1B, for a 30 keV gallium ion beam incident on a platinum sample at an angle of 5° to a surface normal, a maximum of 6 vacancies per incident ion per Angstrom are created, so that a 10 nm thick damage layer is formed on each side of the lamellar sample. If the sample is 50 nm thick, for example, then approximately 40% of the entire sample thickness consists of amorphized and/or damaged and/or contaminated material. Measurements performed on such a sample would likely not reflect the true structure or composition of the bulk material due to the irregularities induced by the gallium ion milling beam.

In some fabrication procedures, the energy of the gallium ion beam can be reduced during the final milling stages in an effort to reduce the amount of damage induced in the sample (e.g., to reduce the mean depth of the induced damage and/or the number of vacancies induced per incident gallium ion). Although sample damage is reduced at lower ion energies, sample milling generally requires more processing time. For certain samples, depending upon the sputtering rate of the ion beam, the additional processing time can be significant.

FIGS. 2A and 2B show simulation results for a 5 keV gallium ion beam incident on a platinum sample at an angle of 5° to a surface normal. Comparing FIG. 2A and FIG. 1A, it is evident that the spatial region of gallium ion penetration—and therefore the spatial region of induced damage in the sample—is smaller at lower gallium ion energies in FIG. 2A. The depth of ion penetration in FIG. 1A is approximately three times larger than the depth of ion penetration in FIG. 2A. Further, as shown in FIG. 2B, vacancies induced in the sample are reduced to approximately 1.4 per incident ion per Angstrom.

Nevertheless, even using lower energy gallium ion means to process samples, the samples still include a relatively large number of defects, including dislocations and other structural inhomogeneities introduced by the gallium ion beam. Measurements performed on such samples are likely to be contaminated by these inhomogeneities, and may not reflect the true structure and composition of the bulk material from which the samples are taken.

To yield samples of higher quality for transmission microscopy applications, it has been discovered that a beam of helium ions can be used in place of the conventional gallium ion beam for sample preparation. The use of helium ions for sample preparation is counterintuitive for at least two reasons. First, due to their relatively small size and mass relative to gallium ions for example, helium ion beams typically mill samples at slower rates than gallium ion beams. As a result, sample fabrication with helium ions requires more time than sample processing with gallium ions of similar energy. Given the fragility of the thin samples, in general, the faster such samples are prepared and transferred to a microscope, the less potential for sample breakage prior to inspection.

Secondly, helium ions typically have greater penetration depths into samples than gallium ions, for example, due to their smaller mass. As a result, the "damage region" in a sample introduced by helium ions, rather than being confined to a relatively thin surface layer of the material as shown in FIGS. 1A and 2A, will instead extend further into the sample, and may extend through the entire thickness of the sample, depending upon the sample's thickness. As a result, while portions of gallium ion-milled samples remain relatively free from dislocations and implanted gallium ions—this damage being confined to surface layers—larger portions of helium ion-milled samples include induced defects and/or implanted helium ions. Such considerations are particularly important for samples with thicknesses of less than 100 nm, for example, such as are commonly investigated using transmission electron and/or ion microscopy.

It has been discovered, however, that although helium ions tend to penetrate deeper into processed samples, the damage induced by the ions is typically smaller than the damage induced by a comparable current of incident gallium ions, because individual helium ions create fewer vacancies in the sample material than even low energy gallium ions. For this reason, high-mean-energy helium ions can be used in place of even low energy gallium ions to fabricate samples, and the amount of sample damage introduced via ion milling processes remains significantly less than the amount of damage induced during gallium ion milling of samples.

FIG. 3 shows a schematic diagram of sample preparation using a helium ion beam. To create a thin lamellar sample, helium ion beam 1130 is incident on a first surface 1170 of material 1100 at an angle θ relative to a surface normal 1140 of material 1100. The angle θ of the helium ion beam is measured based on the central axis 1180 of beam 1130.

Helium ion beam 1130 mills a first channel 1110 in the surface of material 1100. First channel 1110 does not extend completely through material 1100; instead, the channel stops before reaching second surface 1190 of the material opposite first surface 1170. Then, in a subsequent step, ion beam 1130 is incident at a second location on first surface 1170, and is used to form second channel 1120 in the surface of material 1100. Second channel 1120 also does not extend completely through material 110. Further, as above, ion beam 1130 is incident at the second location on further surface 1170 at an angle θ relative to surface normal 1140.

Formation of channels 1110 and 1120 in first surface 1170 of material 1100 yields a small region of material 1150 that remains attached at position 1160 to the bulk portion of material 1100. Measured in a direction orthogonal to surface normal 1140, region 1150—which corresponds to the sample—has a thickness t.

To perform measurements on the thinned sample 1150, the sample is detached or "lifted out" from material 1100. A variety of different methods can be used to perform lift out of the sample. In some embodiments, for example, an extended member such as a needle fabricated from glass or from a metal such as tungsten can be used to contact sample 1150. By applying a relatively small amount of force to sample 1150, the connection between sample 1150 and the result of material 1100 at position 1160 can be severed. The detached sample 1150 can then be removed using the needle and transferred, for example, to a carbon-based grid material in preparation for transmission electron microscopy imaging. Methods for lifting out lamellar microscopy samples and for mounting such samples for transmission microscopy investigation are disclosed, for example, in the following references, the entire contents of which are incorporated herein by reference: Jian Li et al., "Recent advances in FIB-TEM specimen preparation techniques," *Materials Characterization* 57(1): 64-70 (2006); and U.S. Pat. No. 6,570,170.

Figure 4A:
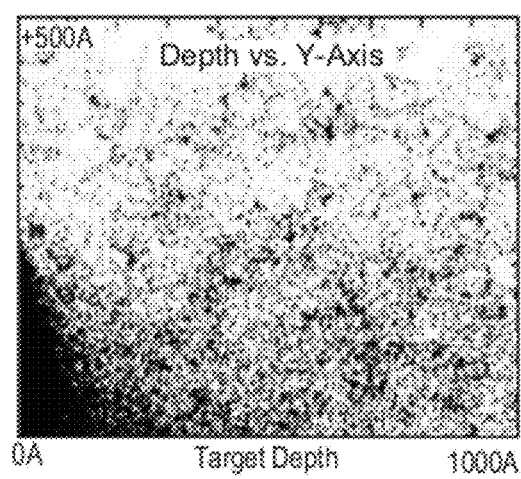
FIG. 4A is a graph showing simulated helium ion beam trajectories in a platinum sample.
Figure 4B:
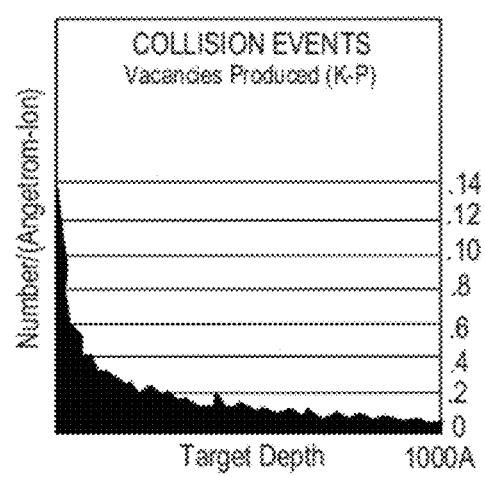
FIG. 4B is a graph showing number of vacancies produced per helium ion per Angstrom as a function of depth for the helium ions of FIG. 4A.

FIGS. 4A and 4B show results of simulations of the ion milling process for a helium ion beam incident on a platinum sample. For these simulations, helium ions having a mean energy of 30 keV were incident at an angle of 5° relative to the surface normal of the platinum material. FIG. 4A shows helium ion penetration as a function of surface position (ordinate) and depth (abscissa). FIG. 4B shows the number of vacancies induced in the sample per incident helium ion per Angstrom. As shown in FIGS. 4A and 4B, although the induced dislocations extend through the entire thickness of the lamellar sample (due to the longer mean penetration depth of helium ions relative to gallium ions), the number of vacancies per incident helium ion is reduced by approximately a factor of 10 relative to the number of vacancies induced by even low energy (e.g., 5 keV) gallium ions. As a result, although induced dislocations are distributed through a larger volume of sample 1150 prepared using the helium ion beam, the defect frequency is substantially reduced, yielding a sample that is better suited for transmission microscopy investigations.

Figures 5A, 5B, 5C:
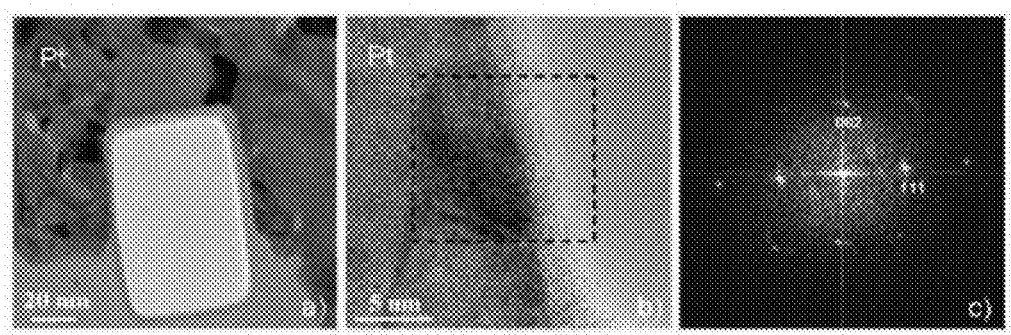
FIG. 5A is an image of a platinum wire that was milled using a helium ion beam.
FIG. 5B is an enlarged image of an edge of the platinum wire of FIG. 5A.
FIG. 5C is an image of detected electrons scattered from the edge of the platinum wire of FIG. 5A.

FIG. 5A shows the results of a cutting operation performed on a 15 nm thick Pt line formed on a 100 nm thick silicon nitride membrane using a helium ion beam. The cutting operation (corresponding to the bright region in FIG. 5A) removed portions of both the Pt and the membrane. Then, the crystal structure of the Pt line was investigated in a region that included the cut (e.g., the dotted region shown in FIG. 5B) using electron microscopy. The scattering pattern of incident electrons is shown in FIG. 5C; the regular pattern of scattering from various planes of the platinum material shows that the crystallinity of the platinum was maintained during helium ion beam cutting. These results show that even in the surface region of the platinum material, the platinum crystal structure is relatively undisturbed by the helium ion beam.

In general, samples can be prepared using the methods and systems disclosed herein in a range of thicknesses. The thickness can be selected to allow a particular fraction of incident electrons to pass through the sample, for detection on the other side of the sample. For example, in some embodiments, the mean thickness t of sample 1150 can be 100 nm or less (e.g., 80 nm or less, 60 nm or less, 50 nm or less, 40 nm or less, 30 nm or less, 20 nm or less, 10 nm or less).

Typically, the helium ion beam is incident at a relatively small angle θ to surface normal 1140 to ensure that the cross-sectional profile of sample 1150 is approximately rectangular. In certain embodiments, for example, the angle θ is 0° or more (e.g., 0.5° or more 1° or more, 2° or more, 3° or more) and/or 20° or less (e.g., 15° or less, 10° or less, 8° or less, 6° or less, 5° or less).

Helium ion beam 1130 typically includes a plurality of helium ions with a distribution of ion energies. The mean energy of the ion beam can be selected to control the average penetration depth and/or milling rate of the ion beam. In some embodiments, the mean energy of the helium ion beam is 25 keV or more (e.g., 30 keV or more, 35 keV or more, 40 keV or more, 45 keV or more, 50 keV or more). The mean energy of the helium ion beam can also be reduced to further reduce the amount of sample damage induced during the milling operation. Although milling at lower ion energies can take longer than milling at higher energies, the sample that is produced can be of higher quality. As will be described in greater detail below, when the energy of the helium ions are reduced, additional agents that participate in chemical reactions with the material being milled can also be introduced. These agents can help to increase the milling rate, offsetting the rate decrease due to the lower ion energy. In certain embodiments, the mean energy of the helium ion beam is 20 keV or less (e.g., 15 keV or less, 10 keV or less, 8 keV or less, 6 keV or less, 5 keV or less, 4 keV or less, 3 keV or less).

Certain samples can be particularly hard to mill using ion beams. In particular, certain materials may not mill cleanly along certain crystal planes, resulting in lamellar samples with jagged, irregular edges. Such samples may be unsuitable for investigation using transmission microscopy.

Figure 6:
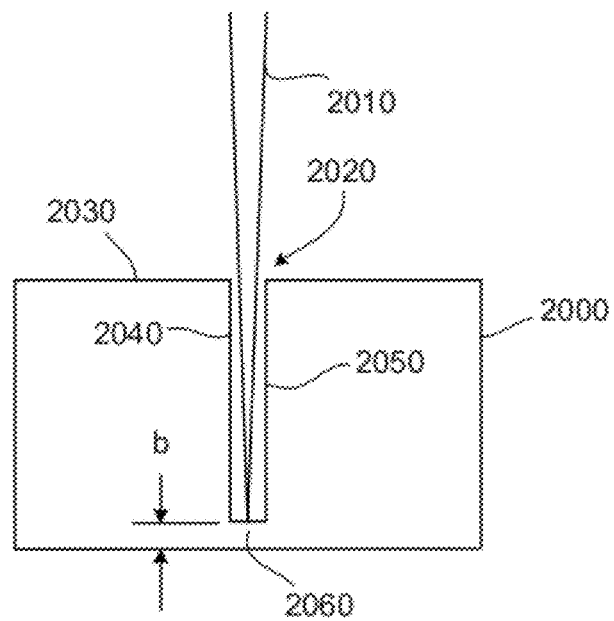
FIG. 6 is a schematic diagram showing a sample that is milled using a helium ion beam.

To prepare thin samples of such materials, top-down sample preparation can be used. FIG. 6 shows a schematic diagram of such a top-down milling procedure. In. FIG. 6, a helium ion beam 2010 is incident on a first surface 2030 of sample 2000. The helium ion beam forms a channel 2020 in sample 2000 having side walls 2040 and 2050, and a bottom wall 2060. Sample 2000 is exposed to beam 2010 to progressively reduce the thickness b of bottom wall 2060.

Top-down milling of the samples generally continues until the thickness b of bottom wall 2060 is reduced to a desired amount. When the desired thickness is reached, exposure to ion beam 2010 is discontinued. Typically, for electron microscopy applications, the thickness b is reduced to 100 nm or less.

The sample being milled can be monitored during fabrication to detect the end-point of the process, at which point exposure is discontinued. In general, helium ion beam 2010 is produced by a helium ion source as part of an ion microscope system. The ion microscope system also includes one or more detectors (see, e.g., detectors 150 and 160 in FIG. 9 discussed later) that detect one or more types of particles that leave the sample during processing. By monitoring signals corresponding to the detection of particles, a control unit connected to the detectors can determine when the desired thickness b of bottom wall 2060 has been reached.

In some embodiments, for example, a detector (e.g., detector 160 in FIG. 9) is positioned below the surface of sample 2000 opposite the surface upon which ion beam 2010 is incident. The detector can be configured to detect incident helium ions that are transmitted through sample 2000. As the thickness b of bottom wall 2060 is reduced, the number of ions that pass through wall 2060 increases, and the ion current measured by the detector also increases.

The control unit connected to the detector can be calibrated with information about transmitted ion currents through different material layer thicknesses. For example, material layers of known thickness can be exposed to helium ions, and the transmitted ion currents for each layer thickness can be measured. This information can be stored in the control unit so that when measurements of the transmitted helium ion current during sample fabrication are transmitted from the detector to the control unit, the control unit can estimate the thickness of the bottom wall based on the stored ion current measurements that are correlated with known material thicknesses. In this manner, the thickness of wall 2060 can be monitored during sample fabrication, and exposure to the helium ion beam can be halted when the desired thickness of the wall is reached.

In certain embodiments, a detector (e.g., detector 150 in FIG. 9) is positioned above the surface of sample 2000 upon which ion beam 2010 is incident. The detector can be configured to detect particles such as secondary electrons that leave sample 2000 in response to the incident helium ions. In general, incident helium ions penetrate a certain depth below the surface of the sample. Secondary electrons are typically generated as a result of the interaction between the incident helium ions and sample atoms. The energies of the secondary electrons depend greatly upon the energies of the helium ions that produce the secondary electrons. Further, as the helium ions penetrate deeper into the sample, they lose energy. As a result, secondary electrons that are generated from interactions between deeply-penetrating helium ions and sample atoms typically have lower energies than secondary electrons generated by interactions that occur between incident ions and sample atoms at shallow depths.

When a plurality of helium ions is incident on a sample, different ions penetrate to different depths within the sample. A detector configured to measure energies of secondary electrons that result from ion-sample interactions therefore measures a distribution of secondary electron energies. Secondary electrons with relatively low energies correspond to deep-penetrating helium ions. Secondary electrons with relatively high energies correspond to shallow-penetrating helium ions. When the thickness of wall 2060 is large compared to the mean penetration depth of the incident helium ions, a distribution of secondary electron energies is measured that corresponds essentially to a complete distribution of penetration depths of helium ions in the sample. The low energy secondary electrons, in particular, correspond to the helium ions that penetrate most deeply.

As the thickness of wall 2060 is reduced, however, some of the helium ions that would otherwise penetrate deeply within the sample before coming to rest instead pass through the sample; that is, the bottom edge of wall 2060 is reached by the ions before the ions have come to rest within the sample. No further secondary electrons are produced when these helium ions leave the sample through the bottom surface of the wall. Accordingly, as the wall thickness is reduced, fewer secondary electrons are produced from deep-penetrating helium ions. The measured energy distribution of the secondary electrons therefore narrows, as there are fewer low energy secondary electrons produced.

The control unit connected to the detector can monitor the width (e.g., the full-width at half-maximum, the width at which the distribution falls to 1/e of its apex value, a width determined by fitting the distribution to a mathematical distribution function, or another metric related to the width) of the secondary electron distribution measured from the sample. The control unit can also be calibrated with stored information about secondary electron energy distributions from samples of different thicknesses. By determining the width of the secondary electron distribution measured by the detector, the control unit can estimate the approximate thickness b of bottom wall 2060. As such, the thickness of wall 2060 can be monitored during sample fabrication by the control unit, and exposure of the sample to the helium ion beam can be discontinued when the desired sample thickness is reached.

Figures 7A, 7B:
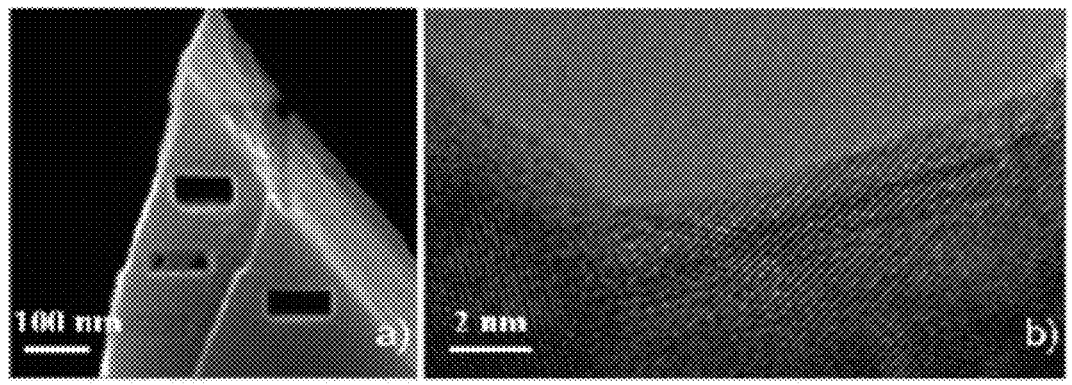
FIG. 7A is a transmission electron microscope image of a crystalline material into which channels were milled using a helium ion beam.
FIG. 7B is an transmission electron microscope image of a bottom wall of one of the channels in the material of FIG. 7A.

FIG. 7A shows a transmission electron microscope image of a wedge-shaped piece of $Cu_xBi_2Se_3$ superconducting crystalline material. This material is typically difficult to thin parallel to the [h k 0] direction (the face of the crystallite) using gallium ion milling, crushing, or microtomy. However, as shown in FIG. 7A, a helium ion beam was used to mill a series of small rectangular channels into the material; as discussed above in connection with FIG. 6, milling was halted in each channel so that the channel did not extend fully through the material.

The material of FIG. 7A was then transferred to an electron microscope system and the high resolution electron microscope image in FIG. 7B was obtained in transmission mode. As shown in FIG. 7B, the $Cu_xBi_2Se_3$ sample was continuous up to the edge, indicating that a relatively small amount of damage to the structure of the material resulted from exposure to the helium ion beam.

Production of such thin sample regions (e.g., the bottom wall of channel 2020) that remain relatively unperturbed and uncontaminated following ion milling is a particularly advantageous and unexpected feature of using a helium ion beam for material preparation. In contrast, when a heavier ion beam such as a gallium ion beam is used for such operations, a significant amount of damage to the bottom wall of the channel occurs. For example, the incident gallium ions tend to exert greater force on the delicate wall membrane, increasing the probability that the membrane will fail mechanically. Further, gallium ion contamination due to implantation is a problem due to the smaller penetration depth of gallium ions relative to helium ions. In contrast, many helium ions—rather than implanting in the bottom wall of the channel—will simply pass right through the bottom wall when it is thin enough. Still further, the number of vacancies in the bottom wall induced by even low energy gallium ions, as explained above in connection with FIGS. 2A and 2B, is approximately an order of magnitude larger than the number of vacancies induced by incident helium ions.

In general, the system parameters discussed above in connection with FIG. 3 are also applicable to FIG. 6. That is, helium ion beam 2010 in FIG. 6 can have the same mean ion energy and angle of incidence discussed above for ion beam 1130. Moreover, the mean thicknesses t disclosed in connection with sample 1150 are also applicable to the mean thickness b of the bottom wall 2060 of channel 2020 in FIG. 6.

In some embodiments, material processing (e.g., ion milling) using helium ions can be combined with beam-induced chemical reactions to further reduce damage induced by the milling process. For example, the rate at which material is removed from channels milled into a material using a helium ion beam can be increased by introducing other agents that react chemically with particles of the material and/or with the incident helium ions. By increasing the rate at which material is removed from the channels using such agents, the helium ion fluence can be reduced, exposing the material to fewer helium ions and further reducing exposure-related damage in the prepared sample. Systems, methods, reagents, and compositions for implementing beam-induced chemical reactions are disclosed, for example, in U.S. Pat. No. 7,485,873, the entire contents of which are incorporated herein by reference.

In certain embodiments, the prepared sample (e.g., sample 1150 and/or sample 2060) can be heated prior to introduction of the sample into a microscope system. For samples such as sample 1150 that are eventually lifted out of bulk material 1100, heating can occur prior to lift-out, following lift-out, or both prior to and post-lift-out. In general, samples can be heated to temperatures that are related to the material from which the samples are formed. By suitably heating the samples, the microscopic structure of the sample remains intact, but the mobility of implanted helium atoms and/or ions is increased. As a result, structural imperfections that are the result of the presence of the implanted atoms and ions can be reduced or eliminated by promoting thermally-induced diffusion of the atoms and/or ions out of the samples. In general, samples can be heated to a temperature of 100° C. or more (e.g., 200° C. or more, 300° C. or more, 500° C. or more, 700° C. or more, 1000° C. or more). Heating can occur for a time period of 1 minute or more (e.g., 2 minutes or more, 5 minutes or more, 10 minutes or more, 20 minutes or more, 30 minutes or more, 1 hour or more, 2 hours or more, 3 hours or more, 5 hours or more, 10 hours or more).

Although the preceding discussion has focused on the use of helium ions for preparation of thin samples, other types of ions can also be used. For example, ion beams used to process samples for transmission microscopy can include a variety of different types of ions. In particular, ion beams can include, in addition to helium ions or as alternatives to helium ions, one or more of argon ions, neon ions, krypton ions, and xenon ions. Typically, any of the many different types of ions that can be generated using the ion beam systems described below can be used to process samples. Further, although in the preceding discussion only one type of ions is mentioned in the ion beams used for sample processing, in certain embodiments the ion beams can include more than one different type of ions.

After the sample is prepared according to one or more of the methods disclosed herein, the sample can be introduced into a microscopy system (e.g., an electron microscopy system or an ion microscopy system) and measurements of various sample properties can be made. In the following discussion, a sample similar to sample 2000 in FIG. 6 is introduced into a transmission electron microscopy system. However, it should be generally understood that samples similar to sample 1150 in FIG. 3 can also be used, and that samples can be introduced into ion microscope systems (e.g., helium ion microscope systems) in addition to, or as an alternative to, electron microscope systems.

Figure 8:
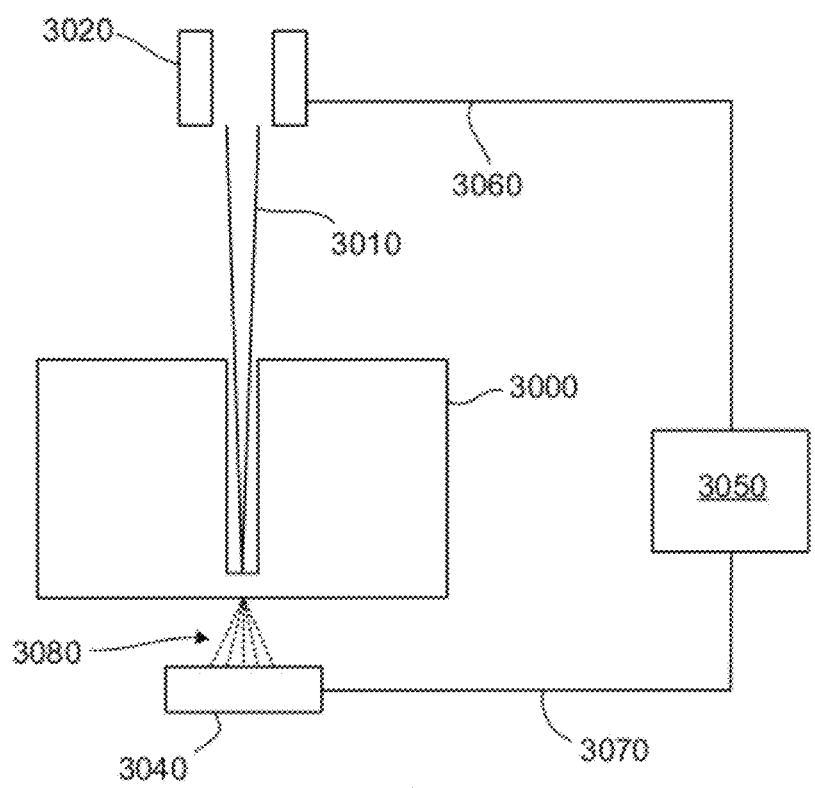
FIG. 8 is a schematic diagram of an electron microscope system.

FIG. 8 shows a schematic diagram of an electron microscope system that includes an electron source 3020, an electron detector 3040, and a control unit 3050 coupled to source 3020 and detector 3040 via control lines 3060 and 3070. During operation, source 3020 directs an electron beam 3010 to be incident on sample 3000 at the region of the thinned bottom wall of the channel formed in the sample. Some of the incident electrons are transmitted through the bottom wall and scatter as they emerge from the solid wall material. Scattered electrons 3080 are detected by detector 3040, and information about the scattered electrons (e.g., positions, energies) is transmitted to control unit 3050.

Control unit 3050 can determine a relatively wide variety of information about sample 3000 based on measurements of scattered electrons 3080. In some embodiments, for example, control unit 3050 can determine structural information (e.g., information about the crystal structure) and/or compositional information about sample 3000.

Methods and systems for performing transmission electron microscopy of thin samples are disclosed, for example, in Stanley L. Flegler, "Scanning and Transmission Electron Microscopy: An Introduction" (Oxford University Press, 1993), the entire contents of which are incorporated herein by reference.

In some embodiments, the helium ion beam used to prepare the samples disclosed herein can be part of a multi-beam instrument. The multi-beam instrument can include, in addition to the helium ion beam used for milling, an electron beam used to measure properties of the sample once it is prepared. For example, FIG. 8 can include a helium ion source coupled to control unit 3050. The helium ion source, under the control of unit 3050, can prepare sample 3000 according to the methods disclosed herein. Once sample preparation is complete, the sample can be exposed to electron beam 3010 for measurement purposes as disclosed above. By using a single instrument for both sample preparation and measurement, the prepared sample does not have to be transferred from one system to another. As a result, accurate position registration between the sample and the instrument can be maintained, and the probability of mechanical handling damage occurring to the sample can be reduced. Further features of multi-beam systems and methods are disclosed, for example, in U.S. Pat. No. 7,485,873.

Ion Beam Systems

The sample preparation methods disclosed herein are implemented using noble gas ion beams such as helium ion beams. In this section, ion beam systems and methods for use in sample preparation are disclosed.

Typically, gas ion beams are produced in multipurpose microscope systems. Microscope systems that use a gas field ion source to generate ions that can be used in material deposition and/or sample analysis (e.g., imaging) are referred to as gas field ion microscopes. A gas field ion source is a device that includes a tip (typically having an apex with 10 or fewer atoms) that can be used to ionize neutral gas species to generate ions (e.g., in the form of an ion beam) by bringing the neutral gas species into the vicinity of the tip (e.g., within a distance of about four to five angstroms) while applying a high positive potential (e.g., one kV or more relative to the extractor (see discussion below)) to the apex of the tip.

Figure 9:
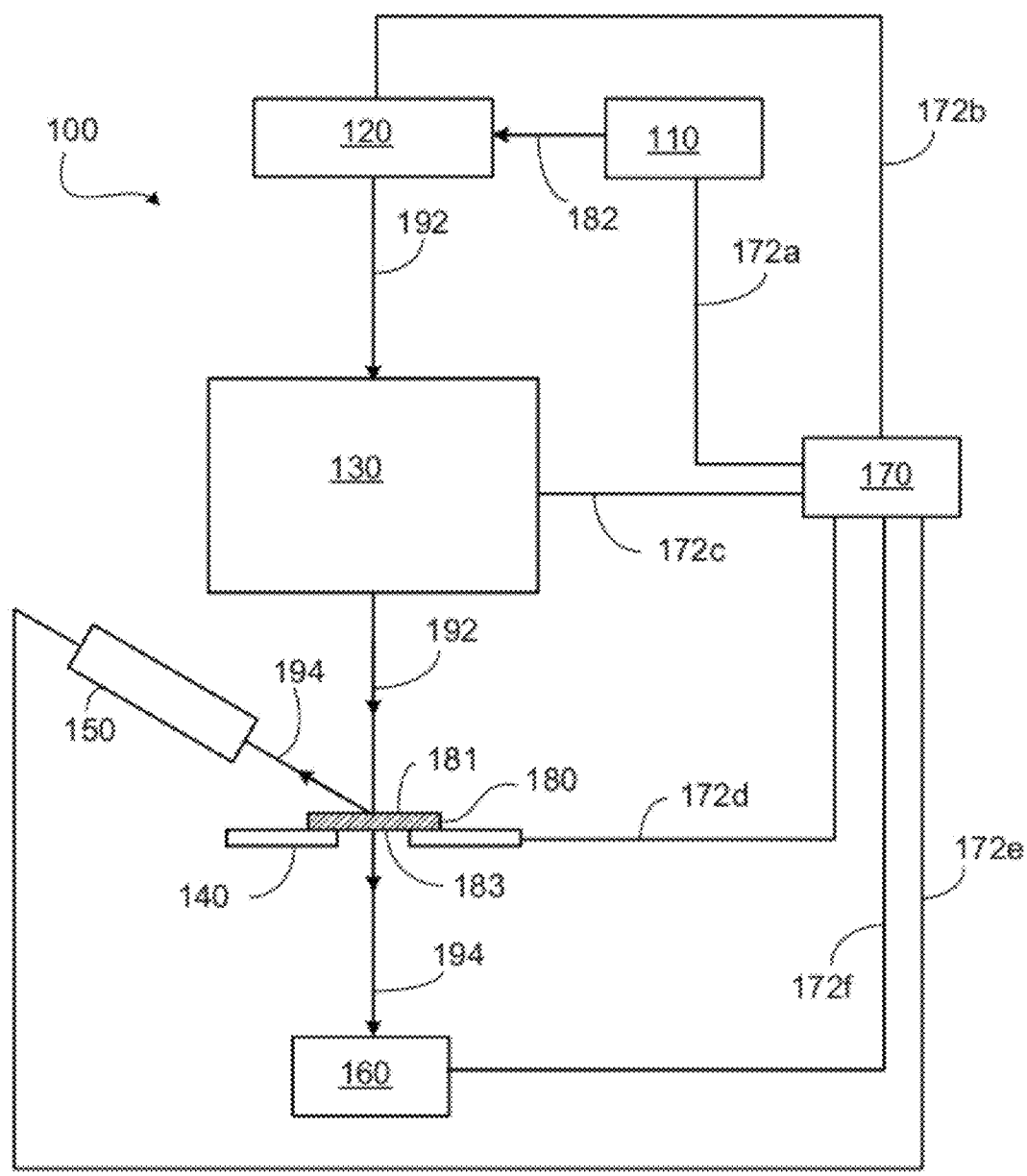
FIG. 9 is a schematic diagram of an ion microscope system.

FIG. 9 shows a schematic diagram of a gas field ion microscope system 100 that includes a gas source 110, a gas field ion source 120, ion optics 130, a sample manipulator 140, a front-side detector 150, a back-side detector 160, and an electronic control system 170 (e.g., an electronic processor, such as a computer) electrically connected to various components of system 100 via communication lines 172a-172f. A sample 180 is positioned in/on sample manipulator 140 between ion optics 130 and detectors 150, 160. During use, an ion beam 192 is directed through ion optics 130 to a surface 181 of sample 180, and particles 194 resulting from the interaction of ion beam 192 with sample 180 are measured by detectors 150 and/or 160.

In general, it is desirable to reduce the presence of certain undesirable chemical species in system 100 by evacuating the system. Typically, different components of system 100 are maintained at different background pressures. For example, gas field ion source 120 can be maintained at a pressure of approximately $10^{-10}$ Torr. When gas is introduced into gas field ion source 120, the background pressure rises to approximately $10^{-5}$ Torr. Ion optics 130 are maintained at a background pressure of approximately $10^{-8}$ Torr prior to the introduction of gas into gas field ion source 120. When gas is introduced, the background pressure in ion optics 130 typically increase to approximately $10^{-7}$ Torr. Sample 180 is positioned within a chamber that is typically maintained at a background pressure of approximately $10^{-6}$ Ton. This pressure does not vary significantly due to the presence or absence of gas in gas field ion source 120.

Figure 10:
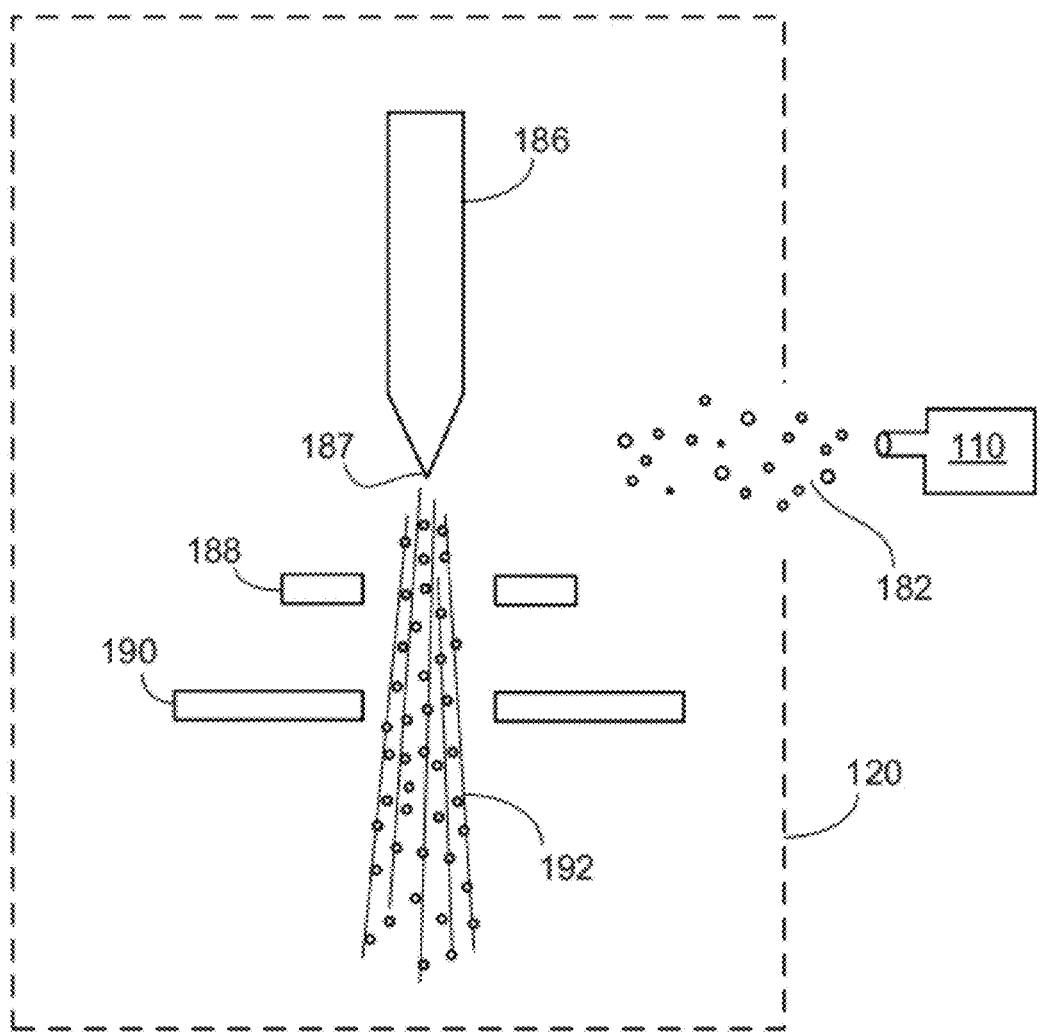
FIG. 10 is a schematic diagram of a gas field ion source.

As shown in FIG. 10, gas source 110 is configured to supply one or more gases 182 to gas field ion source 120. As described in more detail below, gas source 110 can be configured to supply the gas(es) at a variety of purities, flow rates, pressures, and temperatures. In general, at least one of the gases supplied by gas source 110 is a noble gas (helium (He), neon (Ne), argon (Ar), krypton (Kr), xenon (Xe)), and ions of the noble gas are desirably the primary constituent in ion beam 192.

Optionally, gas source 110 can supply one or more gases in addition to the noble gas(es). As discussed in more detail below, an example of such a gas is nitrogen. Typically, while the additional gas(es) can be present at levels above the level of impurities in the noble gas(es), the additional gas(es) still constitute minority components of the overall gas mixture introduced by gas source 110. As an example, in embodiments in which He gas and Ne gas are introduced by gas source 110 into gas field ion source 120, the overall gas mixture can include 20% or less (e.g., 15% or less, 12% or less) Ne, and/or 1% or more (e.g., 3% or more, 8% or more) Ne. For example, in embodiments in which He gas and Ne gas are introduced by gas source 110, the overall gas mixture can include from 5% to 15% (e.g., from 8% to 12%, from 9% to 11%) Ne. As another example, in embodiments in which He gas and nitrogen gas are introduced by gas source 110, the overall gas mixture can include 1% or less (e.g., 0.5% or less, 0.1% or less) nitrogen, and/or 0.01% or more (e.g., 0.05% or more) nitrogen. For example, in embodiments in which He gas and nitrogen gas are introduced by gas source 110, the overall gas mixture can include from 0.01% to 1% (e.g., from 0.05% to 0.5%, from 0.08 to 0.12%) nitrogen. In some embodiments, the additional gas(es) are mixed with the noble gas(es) before entering system 100 (e.g., via the use of a gas manifold that mixes the gases and then delivers the mixture into system 100 through a single inlet). In certain embodiments, the additional gas(es) are not mixed with the noble gas(es) before entering system 100 (e.g., a separate inlet is used for inputting each gas into system 100, but the separate inlets are sufficiently close that the gases become mixed before interacting with any of the elements in gas field ion source 120).

Gas field ion source 120 is configured to receive the one or more gases 182 from gas source 110 and to produce gas ions from gas(es) 182. Gas field ion source 120 includes a tip 186 with a tip apex 187, an extractor 190 and optionally a suppressor 188. Typically, the distance from tip apex 187 to surface 181 of sample 180 (not shown in FIG. 10) is five cm or more (e.g., 10 cm or more, 15 cm or more, 20 cm or more, 25 cm or more), and/or 100 cm or less (e.g., 80 cm or less, 60 cm or less, 50 cm or less). For example, in some embodiments, the distance from tip apex 187 to surface 181 of sample 180 is from five cm to 100 cm (e.g., from 25 cm to 75 cm, from 40 cm to 60 cm, from 45 cm to 55 cm).

Tip 186 can be formed of various materials. In some embodiments, tip 186 is formed of a metal (e.g., tungsten (W), tantalum (Ta), iridium (Ir), rhenium (Rh), niobium (Nb), platinum (Pt), molybdenum (Mo)). In certain embodiments, tip 186 can be formed of an alloy. In some embodiments, tip 186 can be formed of a different material (e.g., carbon (C)).

During use, tip 186 is biased positively (e.g., approximately 20 kV) with respect to extractor 190, extractor 190 is negatively or positively biased (e.g., from −20 kV to +50 kV) with respect to an external ground, and optional suppressor 188 is biased positively or negatively (e.g., from −5 kV to +5 kV) with respect to tip 186. Because tip 186 is typically formed of an electrically conductive material, the electric field of tip 186 at tip apex 187 points outward from the surface of tip apex 187. Due to the shape of tip 186, the electric field is strongest in the vicinity of tip apex 187. The strength of the electric field of tip 186 can be adjusted, for example, by changing the positive voltage applied to tip 186. With this configuration, un-ionized gas atoms 182 supplied by gas source 110 are ionized and become positively-charged ions in the vicinity of tip apex 187. The positively-charged ions are simultaneously repelled by positively charged tip 186 and attracted by negatively charged extractor 190 such that the positively-charged ions are directed from tip 186 into ion optics 130 as ion beam 192. Suppressor 188 assists in controlling the overall electric field between tip 186 and extractor 190 and, therefore, the trajectories of the positively-charged ions from tip 186 to ion optics 130. In general, the overall electric field between tip 186 and extractor 190 can be adjusted to control the rate at which positively-charged ions are produced at tip apex 187, and the efficiency with which the positively-charged ions are transported from tip 186 to ion optics 130.

In general, ion optics 130 are configured to direct ion beam 192 onto surface 181 of sample 180. As described in more detail below, ion optics 130 can, for example, focus, collimate, deflect, accelerate, and/or decelerate ions in beam 192. Ion optics 130 can also allow only a portion of the ions in ion beam 192 to pass through ion optics 130. Generally, ion optics 130 include a variety of electrostatic and other ion optical elements that are configured as desired. By manipulating the electric field strengths of one or more components (e.g., electrostatic deflectors) in ion optics 130, He ion beam 192 can be scanned across surface 181 of sample 180. For example, ion optics 130 can include two deflectors that deflect ion beam 192 in two orthogonal directions. The deflectors can have varying electric field strengths such that ion beam 192 is rastered across a region of surface 181.

Referring to FIG. 9, in some embodiments, sample manipulator 140 can be biased, either positively or negatively with respect to a common external ground, by applying a relatively small electrical potential to manipulator 140. For example, in some embodiments, a positive potential bias of 5 V or more (e.g., 10 V or more, 20 V or more, 30 V or more, 40 V or more, 50 V or more) relative to the common external ground can be applied to manipulator 140 to assist in preventing positively charged He ions from adhering to surface 181 of sample 180. In certain embodiments, a negative potential bias of −200 V or more (e.g., −150 V or more, −100 V or more, −50 V or more, −40 V or more, −30 V or more, −20 V or more, −10 V or more, −5 V or more) relative to the common external ground can be applied to manipulator 140 to assist, for example, in accelerating secondary electrons (that leave surface 181 of sample 180 via the interaction of the ions with sample 180) away from the sample, ensuring that the secondary electrons can be detected by a suitably configured detector. In general, the potential applied to manipulator 140 can be chosen as desired according to the particular material under study, the He ion current, and exposure time of the sample.

In general, when He ions are incident on a surface of a sample, secondary electrons leave the sample, resulting in the surface having a net positive charge. Excess positive charges on the surface of the sample can produce a number of undesirable effects. In some embodiments, the material of the sample can be damaged by the positive charges. For example, certain materials are charge sensitive, and can react violently (e.g., explode) in the presence of excess positive (or negative) charge. Further, positive charging of the surface of the sample can cause inaccurate ion beam rastering. Deflection and deceleration of the incident ion beam as a result of the electric field created by positive charges at the surface of the sample can reduce the energy of the incident ions, and change their trajectories in difficult-to-predict fashion. If the net positive charge on the surface of the sample becomes large enough, the surface of the sample can act as an electrostatic mirror for He ions, deflecting He ions away from the surface of the sample before the He ions reach the surface of the sample.

In some embodiments, a flood gun capable of delivering a flux of electrons to the surface of the sample can be used to counteract surface charging effects. The electron flux on surface 181 can, in general, be controlled so that surface charging effects are counterbalanced by the electrons supplied by the flood gun.

In some embodiments, both the He ion beam and the beam of electrons from the flood gun can simultaneously impinge on surface 181 of sample 180. In certain embodiments, electrons can be delivered to sample 180 using different methods. For example, prior to exposing surface 181 to He ion beam 192, a flood gun connected to control system 170 can be configured to deliver an electron beam to sample 180 to create a charge layer in a sub-surface region of sample 180.

When incident on surface 181, the average energy of the electrons supplied by a flood gun can be 500 eV or more (e.g., 1 keV or more, 2 keV or more), and/or 20 keV or less (e.g., 15 keV or less, 10 keV or less). For example, when incident on surface 181, the average energy of the electrons can be from 500 eV to 20 keV (e.g., from 1 keV to 15 keV, from 2 keV to 10 keV).

In certain embodiments, the total current of electrons delivered to sample 180 by the flood gun is 10 pA or more (e.g., 100 pA or more, 1 nA or more, 10 nA or more), and/or 100 μA or less (e.g., 10 μA or less, 1 μA or less, 500 nA or less, 100 nA or less). For example, the total current of electrons delivered to sample 180 can be from 10 pA to 1 μA (e.g., from 100 pA to 100 nA, from 1 nA to 10 nA).

In some embodiments, a flood gun can be configured to deliver electrons to sample 180 which have a negative landing energy—that is, in the absence of positive charge on the sample surface, electrons that do not land at all on surface 181. When sample 180 acquires surface charge due to incident He ions, electrons from the flood gun begin to land on surface 181, neutralizing the positive charge. As a result, surface 181 of sample 180 is maintained in an approximately uncharged state.

When ion beam 192 impinges on sample 180, a variety of different types of particles 194 can be produced. These particles include, for example, secondary electrons, Auger electrons, secondary ions, secondary neutral particles, primary neutral particles, scattered ions and photons (e.g., X-ray photons, IR photons, visible photons, UV photons). Detectors 150 and 160 are positioned and configured to each measure one or more different types of particles resulting from the interaction between He ion beam 192 and sample 180. As shown in FIG. 9, detector 150 is positioned to detect particles 194 that originate primarily from surface 181 of sample 180, and detector 160 is positioned to detect particles 194 that emerge primarily from surface 183 of sample 180 (e.g., transmitted particles). As described in more detail below, in general, any number and configuration of detectors can be used in the microscope systems disclosed herein.

In some embodiments, multiple detectors are used, and some of the multiple detectors are configured to measure different types of particles. In certain embodiments, the detectors are configured to provide different information about the same type of particle (e.g., energy of a particle, angular distribution of a given particle, total abundance of a given particle). Optionally, combinations of such detector arrangements can be used.

In general, the information measured by the detectors is used to determine information about sample 180. Typically, this information is determined by obtaining one or more images of sample 180. By rastering ion beam 192 across surface 181, pixel-by-pixel information about sample 180 can be obtained in discrete steps. Detectors 150 and/or 160 can be configured to detect one or more different types of particles 194 at each pixel. Typically, a pixel is a square, although in some embodiments, pixels can have different shapes (e.g., rectangular). A pixel size, which corresponds to a length of a side of the pixel, can be, for example, from 100 pm to two µm (e.g., from one nm to one µm). In some embodiments, the location of adjacent pixels can be determined to within at least 200 pm (e.g., to within at least 100 pm, to within at least 75 pm, to within at least 50 pm). Thus, the operator of the system can determine the location of the center of the beam spot to within at least 200 pm (e.g., to within at least 100 pm, to within at least 75 pm, to within at least 50 pm). In certain embodiments, the field of view (FOV) of sample 180 is 200 nm or more (e.g., 500 nm or more, 1 µm or more, 50 µm or more, 100 µm or more, 500 µm or more, 1 mm or more, 1.5 mm or more), and/or 25 mm or less (15 mm or less, 10 mm or less, five mm or less). The field of view refers to the area of a sample surface that is imaged by the ion microscope.

The operation of microscope system 100 is typically controlled via electronic control system 170. For example, electronic control system 170 can be configured to control the gas(es) supplied by gas source 110, the temperature of tip 186, the electrical potential of tip 186, the electrical potential of extractor 190, the electrical potential of suppressor 188, the settings of the components of ion optics 130, the position of sample manipulator 140, and/or the location and settings of detectors 150 and 160. Optionally, one or more of these parameters may be manually controlled (e.g., via a user interface integral with electronic control system 170). Additionally or alternatively, electronic control system 170 can be used (e.g., via an electronic processor, such as a computer) to analyze the information collected by detectors 150 and 160 and to provide information about sample 180 (e.g., topography information, material constituent information, crystalline information, voltage contrast information, optical property information, magnetic information), which can optionally be in the form of an image, a graph, a table, a spreadsheet, or the like. Typically, electronic control system 170 includes a user interface that features a display or other kind of output device, an input device, and a storage medium.

In certain embodiments, electronic control system 170 can be configured to control various properties of ion beam 192. For example, control system 170 can control a composition of ion beam 192 by regulating the flow of gases into gas field ion source 120. By adjusting various potentials in ion source 120 and ion optics 130, control system 170 can control other properties of ion beam 192 such as the position of the ion beam on sample 180, and the average energy of the incident ions. As disclosed above, control system 170 can also be configured to control a gas injection sub-system for delivering one or more precursor gases in the vicinity of the location where ion beam 192 is incident upon sample 180. Control of the gas injection sub-system can be synchronized with control of the position of ion beam 192 on sample 180, for example.

Detectors 150 and 160 are depicted schematically in FIG. 9, with detector 150 positioned to detect particles from surface 181 of sample 180 (the surface on which the ion beam impinges), and detector 160 positioned to detect particles from surface 183 of sample 180. In general, a wide variety of different detectors can be employed in microscope system 100 to detect different particles, and a microscope system 100 can typically include any desired number of detectors. The configuration of the various detector(s) can be selected in accordance with particles to be measured and the measurement conditions. In some embodiments, a spectrally resolved detector may be used. Such detectors are capable of detecting particles of different energy and/or wavelength, and resolving the particles based on the energy and/or wavelength of each detected particles. In certain embodiments, a spectrally resolved detector includes components capable of directing particles to different regions of the detector based on the energy and/or wavelength of the particle.

In general, detectors 150 and/or 160 can include any one or more of the following detector types: Everhart-Thornley (ET) detectors, which can be used to detect secondary electrons, ions, and/or neutral particles; microchannel plate detectors, which can be used to amplify a flux of secondary electrons, neutral atoms, or ions from a sample; conversion plates, which can be used to detect ions (e.g., scattered ions, secondary ions) from a sample or neutral particles (e.g., primary neutral He atoms) from the sample; channeltron detectors, which can be used to detect particles such as electrons, ions and neutral atoms leaving a sample; phosphor-based detectors, which include a thin layer of a phosphor material deposited atop a transparent substrate, and a photon detector such as a CCD camera, a PMT, or one or more diodes, and which can be used to detect electrons, ions and/or neutral particles from a sample; solid state detectors, which can be used to detect secondary electrons, ions, and/or neutral atoms from a sample; scintillator-based detectors, which include a scintillator material that generates photons in response to being struck by an incident particle (electron, ion, or neutral atom), which can be particularly useful for energy measurements of particles; electrostatic and magnetic prism detectors for ions and electrons; quadrupole detectors for ions; biased particle selectors for ions and electrons; time-of-flight detectors for secondary electrons, ions, and neutral atoms; and angle-resolving detectors that can measure angle-dependent scattering information for ions, electrons, and neutral atoms.

Computer Hardware and Software

In general, any of the methods described above can be implemented in computer hardware or software, or a combination of both. In particular, methods relating to the preparation of samples can be implemented in computer hardware and/or software. The methods can be implemented in computer programs using standard programming techniques following the methods and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The methods can also be implemented as a computer-readable storage medium, configured with a computer program, where the storage medium so configured causes a computer to operate in a specific and predefined manner to perform the functions described herein.

OTHER EMBODIMENTS

Other embodiments are in the claims.

What is claimed is:

1. A method of preparing a sample, comprising:
   forming a first channel in a material by directing a first plurality of noble gas ions at the material, the first channel having a first side wall and a second side wall;
   forming a second channel in the material by directing a second plurality of noble gas ions at the material, the second channel having a third side wall and a fourth side wall, wherein the second channel is spaced from the first channel so that a portion of the material between channels has parallel walls and a mean thickness of 100 nm or less between the parallel walls; and
   detaching the portion from the material to yield the sample.

2. The method of claim 1, wherein the sample is a transmission microscopy sample.

3. The method of claim 1, wherein the first plurality of noble gas ions is incident on the material at an angle of 10 degrees or less relative to a surface normal of the material.

4. The method of claim 3, wherein the first plurality of noble gas ions is incident on the material at an angle of 5 degrees or less relative to the surface normal of the material.

5. The method of claim 1, wherein the mean thickness of the sample is 50 nm or less.

6. The method of claim 1, wherein a mean energy of the first plurality of noble gas ions is 30 keV or more.

7. The method of claim 1, wherein a mean energy of the second plurality of noble gas ions is 30 keV or more.

8. The method of claim 1, wherein a mean energy of the second plurality of noble gas ions is 15 keV or less.

9. The method of claim 1, wherein detaching the portion from the material comprises contacting a first region of the portion with an extended member.

10. The method of claim 1, further comprising contacting the detached portion with a carbon-based grid material.

11. The method of claim 1, further comprising heating the material prior to detaching the portion.

12. A method of preparing a sample, comprising:
    exposing a material to noble gas ions by directing a plurality of the noble gas ions at the material to form a channel in the material, the channel having a bottom wall oriented in a plane perpendicular to a direction of incidence of the noble gas ions on the material; and
    stopping the exposing when a mean thickness of the bottom wall of the channel, measured in a direction parallel to the direction of incidence, is less than 100 nm, wherein a width of the channel is smaller than a depth of the channel, the width of the channel being perpendicular to the direction of incidence, and the depth of the channel being parallel to the direction of incidence.

13. The method of claim 12, wherein the mean thickness of the bottom wall is less than 50 nm.

14. The method of claim 12, wherein the plurality of noble gas ions is incident on the material at an angle of 10 degrees or less relative to a surface normal of the material.

15. The method of claim 12, wherein a mean energy of the plurality of noble gas ions is 30 keV or more.

16. The method of claim 12, wherein a mean energy of the plurality of noble gas ions is 15 keV or less.

17. The method of claim 12, further comprising positioning the material on a carbon-based grid material.

18. The method of claim 12, further comprising monitoring the mean thickness of the bottom wall during the exposing.

19. A method, comprising:
    using a noble gas ion beam to form a first channel and a second channel in a surface of a material, a portion of the material positioned between the channels having parallel walls and a mean thickness of 100 nm or less between the parallel walls;
    detaching the portion of the material;
    exposing a first surface of the detached portion to a plurality of charged particles; and
    detecting particles leaving a second surface of the detached portion opposite to the first surface, wherein:
    the first channel has a first side wall and a second side wall and the second channel has a third side wall and a fourth side wall.

20. A method, comprising:
    using a noble gas ion beam to form a channel in a surface of a material, the channel comprising a bottom wall with a mean thickness of 100 nm or less;
    exposing a first surface of the bottom wall to a plurality of charged particles; and
    detecting particles leaving a second surface of the bottom wall opposite to the first surface, wherein a width of the channel is smaller than a depth of the channel, the width of the channel being perpendicular to a direction of incidence of the noble gas ion beam on the material, and the depth of the channel being parallel to the direction of incidence.

* * * * *

UNITED STATES PATENT AND TRADEMARK OFFICE
CERTIFICATE OF CORRECTION

| | | |
|---|---|---|
| PATENT NO. | : 8,624,185 B2 | Page 1 of 1 |
| APPLICATION NO. | : 13/233397 | |
| DATED | : January 7, 2014 | |
| INVENTOR(S) | : Diederik Jan Maas et al. | |

It is certified that error appears in the above-identified patent and that said Letters Patent is hereby corrected as shown below:

Title Page, Col. 2 item (56), (Other Publications), line 5, delete "Left." and insert -- Lett. --.

In the Specification

Col. 12, line 8, delete "$10^{-6}$ Ton." and insert -- $10^{-6}$ Torr. --.

Signed and Sealed this
Thirteenth Day of May, 2014

Michelle K. Lee
*Deputy Director of the United States Patent and Trademark Office*